United States Patent
Wang et al.

(10) Patent No.: US 9,498,321 B2
(45) Date of Patent: *Nov. 22, 2016

(54) DRUG DELIVERY DEVICE FOR PERIPHERAL ARTERY DISEASE

(71) Applicant: Abbott Cardiovascular Systems Inc., Santa Clara, CA (US)

(72) Inventors: Yunbing Wang, Sunnyvale, CA (US); James Oberhauser, Saratoga, CA (US); Manish Gada, Santa Clara, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/042,045

(22) Filed: Feb. 11, 2016

(65) Prior Publication Data

US 2016/0157988 A1      Jun. 9, 2016

Related U.S. Application Data

(63) Continuation of application No. 13/802,098, filed on Mar. 13, 2013, now Pat. No. 9,277,983.

(51) Int. Cl.
*A61F 2/06* (2013.01)
*A61F 2/00* (2006.01)
*A61L 31/04* (2006.01)
*A61L 31/14* (2006.01)
*A61L 31/16* (2006.01)
*A61L 31/12* (2006.01)

(52) U.S. Cl.
CPC ............... *A61F 2/06* (2013.01); *A61L 31/041* (2013.01); *A61L 31/129* (2013.01); *A61L 31/148* (2013.01); *A61L 31/16* (2013.01); *A61L 2300/422* (2013.01)

(58) Field of Classification Search
None
See application file for complete search history.

(56) References Cited

U.S. PATENT DOCUMENTS

2003/0208259 A1* 11/2003 Penhasi ............. A61L 31/148
623/1.15

* cited by examiner

*Primary Examiner* — Jeffrey T Palenik
(74) *Attorney, Agent, or Firm* — Squire Patton Boggs (US) LLP (57) ABSTRACT

A medical device implantable within a peripheral vessel of the body composed of a bioresorbable polymer is disclosed. The device has a high resistance to fracture, is very flexible, and has a high crush recovery when subjected to crushing, axial, or torsional forces.

16 Claims, 1 Drawing Sheet

FIG. 1

DRUG DELIVERY DEVICE FOR PERIPHERAL ARTERY DISEASE

This application is a continuation of U.S. application Ser. No. 13/802,098 filed Mar. 13, 2013 and is incorporated herein by reference.

BACKGROUND OF THE INVENTION

Field of the Invention

This invention relates polymeric medical devices, in particular, bioresorbable stents or stent scaffoldings.

Description of the State of the Art

This invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. A medicated stent may be fabricated by coating the surface of either a metallic or polymeric scaffold with a polymeric carrier that includes an active or bioactive agent or drug. Polymeric scaffolds may also serve as a carrier of an active agent or drug. An active agent or drug may also be included on a scaffold without being incorporated into a polymeric carrier.

The stent are generally made to withstand the structural loads, namely radial compressive forces, imposed on the scaffold as it supports the walls of a vessel. Therefore, a stent must possess adequate radial strength. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading or pressure, which if exceeded, creates a yield stress condition resulting in the stent diameter not returning to its unloaded diameter, i.e., there is irrecoverable deformation of the stent. See, T. W. Duerig et al., Min Invas Ther & Allied Technol 2000: 9(3/4) 235-246. Stiffness is a measure of the elastic response of a device to an applied load and thus will reflect the effectiveness of the stent in resisting diameter loss due to vessel recoil and other mechanical events. Radial stiffness can be defined of a tubular device such as stent as the hoop force per unit length (of the device) required to elastically change its diameter. The inverse or reciprocal of radial stiffness may be referred to as the compliance. See, T. W. Duerig et al., Min Invas Ther & Allied Technol 2000: 9(3/4) 235-246.

When the radial yield strength is exceeded the stent is expected to yield more severely and only a minimal force is required to cause major deformation. Radial strength is measured either by applying a compressive load to a stent between flat plates or by applying an inwardly-directed radial load to the stent.

Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

Some treatments with stents require its presence for only a limited period of time. Once treatment is complete, which may include structural tissue support and/or drug delivery, it may be desirable for the stent to be removed or disappear from the treatment location. One way of having a stent disappear may be by fabricating a stent in whole or in part from materials that erodes or disintegrate through exposure to conditions within the body. Stents fabricated from biodegradable, bioabsorbable, bioresorbable, and/or bioerodable materials such as bioabsorbable polymers can be designed to completely erode only after the clinical need for them has ended.

To treat peripheral vascular disease percutaneously in the lower limbs is a challenge with current technologies. Long term results are sub-optimal due to chronic injury caused by the constant motions of the vessel and the implant as part of every day life situations. To reduce the chronic injury a bioresorbable scaffold for the superficial femoral artery (SFA) and/or the popliteal artery can be used so that the scaffold disappears before it causes any significant long term damage. However, one of the challenges with the development of a femoral scaffold and especially a longer length scaffold (4-25 cm) to be exposed to the distal femoral artery and potentially the popliteal artery is the presence of fatigue motions that may lead to chronic recoil and strut fractures especially in the superficial femoral artery, prior to the intended bioresorption time especially when implanted in the superficial femoral artery.

A scaffold in the SFA and/or the popliteal artery is subjected to various non-pulsatile forces, such as radial compression, torsion, flexion, and axial extension and compression. These forces place a high demand on the scaffold mechanical performance and can make the scaffold more susceptible to fracture than less demanding anatomies. Stents or scaffolds for peripheral vessels such as the SFA, require a high degree of crush recovery. The term "crush recovery" is used to describe how the scaffold recovers from a pinch or crush load, while the term "crush resistance" is used to describe the force required to cause a permanent deformation of a scaffold. It has been believed that a requirement of a stent for SFA treatment is a radial strength high enough to maintain a vessel at an expanded diameter. A stent with combines such high radial strength, high crush recovery, and high resistance to fracture is a great challenge.

A favorable outcome for vascular intervention is the long-term maintaining of a healthy vessel diameter at the point of intervention. Therefore, an important goal for treatment of the SFA and/or the popliteal artery is the development of bioabsorbable stent with high crush recovery and high resistance to fracture that achieves this goal.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if each said individual publication, patent, or patent application was fully set forth, including any figures, herein.

SUMMARY OF THE INVENTION

Embodiments of the invention include a medical device implantable within a peripheral vessel of the body, comprising a cylindrical radially expandable body formed from a polymer formulation comprising a bioresorbable elastic material greater than 60 wt % of the body and a bioresorbable rigid material less than 40 wt % of the body which form rigid domains dispersed throughout a matrix of the elastic material, and an anti-restenosis drug associated with the body for delivery to the vessel upon implantation of the medical device in the peripheral vessel, wherein the elastic material has a glass transition temperature (Tg) <25 deg C. and the rigid polymer or segment has a Tg greater than 37 deg C., and wherein the body is configured to be expanded from a crimped state to an expanded state within the peripheral vessel in contact with the vessel wall.

Embodiments of the invention include a medical device implantable within a peripheral vessel of the body, comprising a cylindrical radially expandable body formed from a polymer formulation comprising a cross-linked elastic material, and an anti-restenosis drug associated with the body for delivery to the vessel upon implantation of the medical device in the peripheral vessel, wherein the elastic material has a glass transition temperature (Tg) <25 deg C. and the rigid polymer or segment has a Tg greater than 37 deg C., and wherein the body is configured to be expanded from a crimped state to an expanded state within the peripheral vessel in contact with the vessel wall.

DETAILED DESCRIPTION OF THE INVENTION

In many treatment applications using stents, such as coronary intervention, stents expand and hold open narrowed portions of blood vessels. To achieve this, the stent must possess a radial strength in an expanded state that is sufficiently high and sustainable to maintain the expanded vessel size for a period of weeks or months. This generally requires a high strength, rigid material. In the case of bioresorbable polymer stents, bioresorbable polymers that are stiff and rigid have been proposed and used in stents for coronary intervention. Such polymers are stiff or rigid under physiological conditions within a human body. These polymers tend to be semicrystalline polymers that have a glass transition temperature (Tg) sufficiently above human body temperature (approximately 37° C.) that the polymer is stiff or rigid at these conditions. Poly(L-lactide) (PLLA) is an example of such a material which remains stiff and rigid at human body temperature which facilitates the ability of a stent to maintain a lumen at or near a deployed diameter.

Such polymers, however, may have a tendency to fail with a brittle fracture mechanism so that fractures develop at a relative low strain meaning they have a relatively low elongation at break. Therefore, a stent made from such high strength, rigid polymers may be susceptible to fracture if subjected to sufficiently high strains repeatedly. For coronary application, due to the small cyclic deformation of vessel, the risk of fracture may be of little or no concern.

However, for peripheral application, due to the constant movement of leg, the requirement of flexibility or resistance to fracture and crush recovery of the device is much higher than the requirement of its stiffness. Specifically, the ability to maintain long term structural integrity and eliminate the probability of fatigue fracture in large-amplitude deformations becomes more important than maintaining acute radial strength and radial stiffness.

An alternative to a drug-delivery stent is an anti-restenosis drug coated balloon (DCB). The DCB attempts to address the elastic recoil of the stretched arterial wall following conventional angioplasty with a drug-free balloon. The recoil of the arterial wall can undo much of what was accomplished by balloon angioplasty which results in restenosis, the re-clogging of the treated artery. In DCB treatment, a coating containing a drug is formed on the exterior of a balloon. When the balloon is inflated at a target site within a vessel, and the balloon walls contact the vessel walls, the drug is released to the vessel walls. In practice, the majority of the drug is released from the surface of the balloon during its inflation, which may be a few seconds to a few minutes. Like angioplasty, the balloon is then removed, leaving the treated vessel wall with no mechanical support.

Recent clinical studies show that vascular intervention with a drug coated balloon (DCB) may be effective for the treatment of peripheral vascular disease. In particular, the SFA of patients were treated with a Paclitaxel-coated balloon. Micari A, et al. J Am Coll Cardiol Intv. 2012;5:331-338. After 1 year of treatment, more than 70% lumen patency remained. This was achieved in spite of the short time drug release provided by the DCB and lack of vessel support after balloon intervention. One hypothesis that can be drawn from this study is that the results can be further improved by long term drug release after the DCB is removed and the residual drug remaining at the site has been released.

Based on the success of DCB and desire to eliminate the susceptibility of a device to fracture of a high strength, rigid stent, the inventors propose an implantable bioresorbable device with a longer time drug release, having good flexibility, good crush recovery, and high fatigue fracture resistance. The proposed device, however, does not necessarily have sufficient radial strength to prevent the diameter change as commercially available drug eluting stents. The proposed device may have sufficient radial strength to provide limited lumen support.

Embodiments of the present invention are a cylindrical, radially expandable device for implantation in peripheral blood vessels, such as the SFA, that incorporates drug(s) for treatment of restenosis. The device has a high resistance to fracture, low radial stiffness, and high crush recovery. The device may also have a very low radial strength. The drugs can include antiproliferative drugs, anti-inflammatory drugs, and others disclosed herein.

In some embodiments, the device may also have relatively low radial strength that is insufficient to provide mechanical support to vessel walls. For example, if the vessel wall has a tendency to move inward after implantation, the device may not have sufficient outward force to prevent the inward movement. In such a case, the inward pressure of the vessel exceeds the radial strength of the device and the device exhibits irrecoverable inward radial deformation. In certain embodiments, the outward force applied by the device may only be sufficient to maintain its position in contact with the vessel walls. Therefore, in such embodiments, the device acts as an elastic lining on the vessel wall for providing sustained drug delivery to the vessel wall.

In other embodiments, the device may have a radial strength that is high enough to provide some mechanical support to the vessel walls. In this case, the device can prevent or reduce the degree of inward movement of the vessel walls since the radial strength exceeds the inward force or pressure of the vessel walls.

However, since the radial stiffness of the device is relatively low, the inward force of the vessel walls may result in a decrease in diameter of the vessel even when the radial strength of the device is higher than the inward pressure of the vessel walls. In this case, the inward deformation of the device is recoverable since it is elastic deformation inward. Due to the recoverable deformation, the device exhibits a chronic outward force at the reduced diameter.

The material properties of the device material and the device properties such as radial strength and radial stiffness will change as the device degrades after implantation. However, as the device decrease, the device will become embedded in endothelial cells. Therefore, as the properties deteriorate and the device losses mechanical integrity and mass the device will not present danger embolic events.

In certain embodiments, the device may be designed such that its initial radial stiffness or compliance is close to, the same, or less than the radial stiffness of the vessel into which is it implanted. For example, the device may have compliance 70 to 90% of the vessel or 100 to 130% of a vessel. The vessel compliance can be taken to be the compliance of a healthy vessel at site of implantation.

In some embodiments, the device is mounted over a delivery balloon at a reduced profile and may be delivered to an implant site and expanded by the balloon to an expanded diameter. The implant site may be a narrowed portion of the artery and the narrowed portion may be expanded by the expansion of the device. The primary purpose of the implanted device is to provide sustained drug delivery and may provide no mechanical support or patency to the lumen at the implant site. Thus, upon delivery, the device and removal of the balloon, the device may not prevent any elastic recoil of the vessel walls. The post-delivery diameter of the vessel may be due entirely to the natural strength of the vessel walls.

The device may be made partially or completely from a biodegradable, bioresorbable, or bioabsorbable polymer. The device may include some biostable polymer. The device may be configured to eventually completely absorb from an implant site. The device may provide drug delivery once implanted, provide no mechanical support to the vessel, and then gradually completely absorb away. The device may be configured to completely erode away within 6 months, 6 to 12 months, 12 to 18 months, 18 months to 2 years, or greater than 2 years.

A completely bioresorbable device may still include some nonbiodegradable elements such as radiopaque markers or particulate additives. A polymer for use in fabricating stent can be biostable, bioresorbable, bioabsorbable, biodegradable, or bioerodable. Biostable refers to polymers that are not biodegradable. The terms biodegradable, bioresorbable, bioabsorbable, and bioerodable are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, hydrolysis and metabolic processes.

A blood vessel may have a tendency to decrease in diameter or recoil right after implantation (i.e., less than about 30 minutes post-implantation) as well as over a period of days, weeks, or months. Once implanted, the device may not have radial strength sufficient to reduce or prevent the immediate or long-term recoil.

In some embodiments, the radial strength of the device is relatively low. The radial strength of the device immediately after expansion to an intended deployment diameter in a vessel may at most be the radial pressure required for the device to maintain contact with vessel wall. The radial strength may be the less than the minimum pressure to prevent smooth muscle movement. The radial strength may be less than 150 mm Hg, 100 to 150 mm Hg, 1 to 10 mm Hg, or less than 100 mm Hg. The radial strength can be based on a diameter of an as-fabricated device prior to crimping and expansion or a device after it has been crimped and expanded to an intended deployment diameter.

In other embodiments, the radial strength can be high enough to provide mechanical support to a vessel and prevent or reduce a decrease in the diameter of the vessel or to high enough to so that the vessel does not cause irrecoverable deformation. In such embodiments, the radial strength can be greater than 200 mm Hg, 200-300 mm Hg, or higher than 300 mm Hg.

The body of the device has a high resistance to fracture that may result from forces on the device imposed during crimping and deployment and after deployment. The body of the device may be made of mostly or completely of a bioabsorbable polymer material or formulation. A majority of the polymer formulation may include a high toughness, elastic material which is an elastic polymer or polymer segments or blocks. The body may be composed of at least 60 wt % of the elastic material in the form of segments, blocks, polymer, or a combination thereof.

The elastic material of the formulation may be characterized by several properties and may have one or any combination such properties. The elastic material may have an elongation at break greater than 30%, 50%, 80%, 100%, 500%, or above 500%. The elastic polymer material may be a flexible material with a modulus of elasticity less than 1.5 GPa, 1 GPa, or 0.5 GPa, or can be 0.5 GPa to 1 GPa at 25 deg C., 37 deg C., or in a range of 25 to 37 deg C. Additionally, the elastic material may have a Tg less than body temperature or 37 deg C., less than 25 deg C., or less than 0 deg C.

The polymer formulation of the device which may make up all or a portion of a device body, may also be characterized by several properties and may have one or any combination such properties. The polymer formulation may have an elongation at break greater than 30%, 50%, 80%, 100%, 500%, or above 500%. The polymer formation may have a modulus of elasticity less than 1.5 GPa, 1 GPa, or 0.5 GPa or 0.5 to 1 GPa at 25 deg C., 37 deg C., or in a range of 25 to 37 deg C.

The device may be made of a material with the elastic material as a matrix and rigid material (rigid polymers or segments) that form rigid domains dispersed throughout the matrix which act as physical cross-linking net points. The elastic matrix provides high flexibility and good fatigue fracture resistance. The rigid domains act as physical cross-linking net points to ensure high crush recovery. The rigid domains may also provide a small amount lumen support. The matrix may have the Tg of the elastic material and the rigid domains may have the Tg of the rigid material.

Rigid domains may include or be composed of rigid polymers or segments such as PLLA and polyglycolide. The rigid domains may have a size (i.e., diameter) of 1 to 5 microns, or 0.1 to 1 microns.

Examples of biodegradable elastic polymers or segments include but are not limited to poly(4-hydroxybutyrate) (P4HB), polycaprolactone (PCL), poly(trimethylene carbonate) (PTMC), poly(butylene succinate) (PBS), poly(p-dioxanone) (PDO). The device material can include blends of elastic polymers with rigid polymers or other elastic polymers, copolymers (block, random or alternating) of elastic polymers with rigid polymers or other elastic polymers, or any combination thereof.

The rigid polymers or segments may be characterized by several properties and may have one or any combination such properties. The rigid polymers or segments may have an elongation at break less than 20%, 10%, 5%, or 3%. The rigid polymers or segments may have a modulus of elasticity greater than 3 GPa, 5 GPa, or 7 GPa. Additionally, the rigid polymers or segments may have a Tg greater than body temperature or 37 deg C., or greater than 10 or greater than 20 deg C. above human body temperature or 37 deg C. The rigid polymers or segments may have one or any combination of such properties.

Other rigid bioresorbable polymers or segments include poly(D-lactide) (PDLA), and poly(L-lactide-co-glycolide) (PLGA). The PLGA includes those having a mole % of (LA:GA) of 85:15 (or a range of 82:18 to 88:12), 95:5 (or a range of 93:7 to 97:3), or commercially available PLGA products identified being 85:15 or 95:5 PLGA.

Drug delivery from the device can be provided from a coating on a surface of the body of the device. The coating may be in the form a neat drug. Alternatively, the coating includes a polymer matrix with the drug mixed or dissolved in the polymer. The polymer matrix can be bioresorbable. Suitable polymers for the drug delivery polymer can include poly(DL-Lactide), polycaprolactone, poly(L-lactide), polyglycolide, or poly(glycolide-co-caprolactone).

The coating can be formed by mixing the polymer and the drug in a solvent and applying the solution to the surface of the device. The drug release rate may be controlled by adjusting the ratio of drug and polymeric coating material. The drug may be released from the coating over a period of one to two weeks, up to one month, or up to three months after implantation. Thickness of the coating on the device body may 1 to 20 microns, 1 to 2 microns, 1 to 5 microns, 2 to 5 microns, 3 to 5 microns, 5 to 10 microns, or 10 to 20 microns. In some embodiments, the body of the device includes a drug release coating and the body is free of drug, aside from any incidental migration of drug into the body from the coating.

Alternatively or additionally, the drug can also be embedded or dispersed into the body of device, and be slowly released up to months (e. g., three months after implantation) and while the device is degrading. In this case, the drug can be included with the polymer when the tube is formed that is used to form the device. For example, the drug can be included in the polymer melt during extrusion or injection molding or in a solution when the tube is formed from dipping or spraying or casting.

There are several embodiments of the device material or polymer formulation that includes the elastic polymer or segments and the rigid polymer or segments.

A first set of embodiments is a polymer blend of an elastic polymer as matrix and copolymer containing rigid segments and elastic segments. The blend can include greater than 60 wt % elastic polymer and less than 40 wt % of the copolymer. The elastic segments of the copolymer act as anchor chains to ensure the compatibility of the copolymer and elastic matrix material, while the rigid segment forming rigid domains that acts as physical cross-linking net points.

The elastic material of the blend can include PCL, PTMC, PDO, and P4HB while the copolymer can be PLLA-PCL, PLLA-PTMC, PLLA-PDO, or PGA-PCL copolymer, where the elastic polymer of the matrix is paired with the copolymer having the elastic polymer as a segment. The copolymer can be either block copolymer or random copolymer. At least some rigid chains should be long enough to form physical crosslinks together.

In this first set of embodiments, the molecular weight (MW) of the elastic material may be greater than 50 kDa, for example, 50 to 100 kDa. The MW of the copolymer may be greater than 50 kDa, for example, 50 to 100 kDa. The MW of rigid and elastic segments of copolymer may both be above 20 kDa, for example, 20 to 80 kDa.

A preferred combination of elastic material and copolymer may be 70 wt % and 30 wt %, respectively, with a range of 60 to 80 wt % and 20 to 40 wt %, respectively. The composition of rigid and elastic segments of copolymer may each be less than 20 wt % of the copolymer.

A second set of embodiments is a polymer blend of bioresorbable elastic polymer as matrix (more than 60 wt %, or 60 to 80 wt %) and rigid polymer forming rigid domains that act as physical cross-linking net points (less than 40 wt % or 20 to 40 wt %). The blend can further include a block copolymer (less than 5 wt %, or 3 to 5 wt %) containing rigid segments and elastic segments as compatibilizer. The copolymer can act as anchor chains to ensure the compatibility of the elastic matrix material and rigid domains. The rigid material acts as physical cross-linking net points and its crystallinity increased though annealing or deformation. The elastic material of the blend can be PCL, PTMC, PDO, P4HB, while the rigid material can be PLLA or PGA. The copolymer can be PLLA-PCL, PLLA-PTMC, PLLA-PDO or PGA-PCL block copolymer, where the copolymer is paired with a blend corresponding to the segments of the copolymer. The blends can be prepared by melt blending or solution blending.

In this second set of embodiments, the MW of the elastic material may be greater than 50 kDa, for example, 50 to 100 kDa. The MW of the rigid material may be greater than 50 kDa, for example, 50 to 100 kDa. The MW of the copolymer may be greater than 50 kDa, for example, 50 to 100 kDa. The MW of rigid and elastic segments of copolymer may both be above 20 kDa, for example, 20 80 kDa. A preferred combination of elastic material, rigid material, and copolymer may be 80 wt %, 17 wt %, and 3 wt %, respectively.

A third set of embodiments is a polymer blend of a bioresorbable elastic copolymer material as matrix (more than 80 wt %, or 80 to 90 wt %), and rigid material forming rigid domains that act as physical cross-linking net points (less than 20 wt %, or 10 to 20 wt %). The rigid segments of the elastic copolymer act as anchor chains to ensure the compatibility of the copolymer matrix and rigid material. The rigid material can be PLLA, PGA, while the copolymer can be PCL-PLLA, PTMC-PLLA, PDO-PLLA or PCL-PGA copolymer, where the rigid polymer is paired with an elastic copolymer with the same rigid polymer component. The elastic copolymer can be either block copolymer or random copolymer.

In the context of a random copolymer, "segment" can refer to a single unit derived from a polymer or several chemical bonded units derived from monomer units. In the context of a block copolymer, "block" can refer to several chemically bonded derived from monomer units having a MW of at least 50 kDa. The elastic segment in the copolymer matrix may be higher than 80 wt %.

In this third set of embodiments, the MW of the elastic copolymer may be greater than 50 kDa, for example, 50 to 100 kDa. The MW of the rigid material may be greater than 50 kDa, for example, 50 to 100 kDa. The MW of rigid and elastic segments of elastic copolymer may both be above 20 kDa, for example, 20 to 80 kDa.

A fourth set of embodiments is a bioresorbable block copolymer with more than 60 wt % elastic segment content and less than 40 wt % crystallized rigid segment forming domains that act as physical cross-linking net points. The copolymer can be, for example, PCL-PLLA, PTMC-PLLA, PDO-PLLA or PCL-PGA copolymer. To ensure that the rigid segment works as physical cross-linking net points, the molecular weight of rigid segment in each block copolymer chain should be higher than its entanglement molecular weight, and preferred to be more than two times higher than its entanglement molecular weight. For PCL-PLLA or PDO-PLLA copolymer, the molecular weight of PLLA segment is preferred to be at least more than 20 kDa. After blending, a tube is formed by, for example, extrusion or solution casting.

In this fourth set of embodiments, the MW of the block copolymer may be greater than 80 kDa, for example, 80 to 100 kDa. The MW of the elastic segment may be above 50 kDa, for example, 50 to 70 kDa and the MW of rigid segment may be above 30 kDa, for example, 30 to 50 kDa.

The above polymer blends can be prepared by melt blending or solution blending. After making the device material, a tube is formed by extrusion, solution casting, dipping, or injection molding.

A fifth set of embodiments is a polymer formulation that includes a crosslinked bioresorbable elastic polymer. A device can be formed from an elastic polymer with reactive end groups or side groups that can form crosslinks upon exposure to heat or radiation. Alternatively, a device can be formed from an elastic polymer including a crosslinking agent that can form crosslinks upon exposure to heat or radiation.

To fabricate the device, a tube may be formed from the elastic polymer by extrusion or solution casting and then is cut by a laser to form a pattern in the tube. After that, crosslinking is initiated high energy e-beam, or by UV light or by heat to form the chemical cross-linking net points. The radiation or heat initiates reaction of the reactive end/side groups with each or initiates the crosslinking by the crosslinking agent.

Alternatively, the crosslinking step can be performed before laser cutting. After crosslinking, the tube may be laser cut.

The types of polymers that can be crosslinked in this manner include PCL, PTMC, PDO or copolymers such as PCL-PLLA or PCL-PGA. The reactive end/side group includes di-iscocynate or di-acrylate groups. Exemplary crosslinking agents include triallyl isocyanurate (TAIC), trimethally isocyanurate (TMAIC), and trimethylolpropane triacrylate (TMPTA). Exemplary methods of making a crosslinked bioresorbable aliphatic polyester are disclosed in US2010-0262223.

The rigid domains may be semicrystalline with a crystallinity of 10 to 50%, 10 to 20%, 20 to 30%, 30 to 40%, 40 to 50%, or greater than 50%. After forming a tube, the crystallinity of the domains may be increased by annealing the tube at a temperature above the Tg of the rigid polymer or segments. Additionally or alternatively, the tube may be radially expanded at a temperature above the Tg of the rigid polymer or segments to increase the crystallinity.

A formed tube may be free or substantially free of holes between the interior and exterior surface. The device can be fabricated from the formed tube with laser cutting which forms a tubular device with structural elements and gaps in the tube wall between the inner and outer surface formed by laser cutting.

The final device can be balloon expandable or self expandable. In the case of a balloon expandable device, the geometry of the device can be an open-cell structure similar to the stent patterns disclosed herein or close cell structure, each formed through laser cutting the tube. In a balloon expandable device, when the device is crimped from a fabricated diameter to a crimped or delivery diameter onto a balloon, structural elements plastically deform. Aside from incidental recoil outward, the device retains a crimped diameter without an inward force on the crimped device due to the plastically deformed structural elements. When the device is expanded by the balloon, the structural elements plastically deform. The device is expanded to an intended expansion or deployment diameter and retains the intended expansion diameter or a diameter slightly less due to incidental recoil inward due to inward pressure from the vessel, stress relaxation, or both. At the final expanded diameter, the device does not exert any chronic outward force, which is a radial outward force exerted by the device in excess of the radial inward force exerted by the vessel on device.

In the case of a self expandable device, when the device is crimped from a fabricated diameter to a crimped or delivery diameter on a balloon, structural elements deform elastically. Therefore, to retain the device at the crimped diameter, the device is restrained in some manner with an inward force, for example with a sheath or a band. The crimped device is expanded to an intended expansion or deployment diameter by removing the inward restraining force which allows the device to self-expand to the intended deployment diameter. The structural elements deform elastically as the device self-expands. If the final expansion diameter is the same as the fabricated diameter, the device does not exert any chronic outward force. If the final expansion diameter is less than the fabricated diameter, the device does exert a chronic outward force. The geometry of the self-expandable device can be a helical construct including a set of spiral coils through laser cutting, or it can also be like a coil through weaving the extruded and annealed fibers.

The geometric structure of the device is not limited to any particular stent pattern or geometry. The device can have the form of a tubular scaffold structure that is composed of a plurality of ring struts and link struts. The ring struts form a plurality of cylindrical rings arranged about the cylindrical axis. The rings are connected by the link struts. The scaffold comprises an open framework of struts and links that define a generally tubular body with gaps in the body defined by the rings and struts.

A thin-walled cylindrical tube of may be formed into this open framework of struts and links described by a laser cutting device that cuts such a pattern into the thin-walled tube that may initially have no gaps in the tube wall. The scaffold may also be fabricated from a sheet by rolling and bonding the sheet to form the tube.

Figure 1:
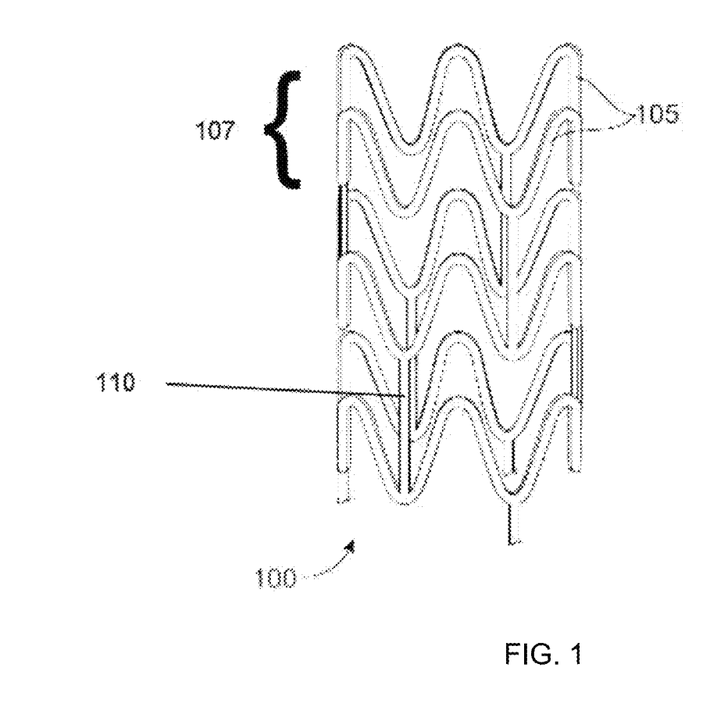
FIG. 1 depicts a view of an exemplary scaffold.

FIG. 1 depicts a view of an exemplary scaffold 100 which includes a pattern or network of interconnecting structural elements 105. FIG. 1 illustrates features that are typical to many stent patterns including cylindrical rings 107 connected by linking elements 110. The cylindrical rings are load bearing in that they provide radially directed force in response to an inward force on the scaffold. The linking elements generally function to hold the cylindrical rings together. Exemplary scaffolds are disclosed in US2008/0275537, US2011/0190872, and US2011/0190871.

The device may have lengths of between 12 and 18 mm, 18 and 36 mm, 36 and 40 mm or even between 40 and 200 mm as fabricated or when implanted in the superficial femoral artery, as an example. The device may have a pre-crimping or as-fabricated diameter of between 5-10 mm, 6-8 mm, or any value between and including these endpoints. The device for may have a wall thickness of about 100 to 150 microns, 150 to 200 microns, 200 to 250 microns, 250 to 300 microns, 300 to 350 microns, 350 to 400 microns, or greater than 400 microns.

The device may be configured for being deployed by a non-compliant or semi-compliant balloon from about a 1.8 to 2.2 mm diameter (e.g., 2 mm) crimped profile. Exemplary balloon sizes include 5 mm, 5.5 mm, 6 mm, 6.5 mm, 7 mm, or 8 mm, where the balloon size refers to a nominal inflated diameter of the balloon. The device may be deployed to a diameter of between 4 mm and 10 mm, 7 to 9 mm, or any value between and including the endpoints. Embodiments of the invention include the device in a crimped diameter over and in contact with a deflated catheter balloon.

The intended deployment diameter may correspond to, but is not limited to, the nominal deployment diameter of a catheter balloon which is configured to expand the scaffold. A device scaffold may be laser cut from a tube (i.e., a pre-cut tube) that is less than an intended deployment diameter. In this case, pre-cut tube diameter may be 0.7 to 1 times the intended deployment diameter or any value in between and including the endpoints.

A device scaffold may be laser cut from a tube (i.e., a pre-cut tube) that is greater than an intended deployment diameter. In this case, the pre-cut tube diameter may be 1 to 1.5 times the intended deployment diameter, or any value in between and including the endpoints.

The device of the present invention has high crush recovery and crush resistance. Crush recovery describes the recovery of a tubular device subjected to a pinch or crush load. Specifically, the crush recovery can be described as the percent recovery to the device pre-crush shape or diameter from a certain percent crushed shape or diameter. Crush resistance is the minimum force required to cause a permanent deformation of a scaffold. The crush recovery and crush resistance can be based on a pre-crush shape or diameter of an as-fabricated device prior to crimping and expansion or a device after it has been crimped and expanded to an intended deployment diameter. The crush recovery of the device can be such that the device attains greater than about 80% or 90% of its diameter after being crushed to at least 50% of its pre-crush diameter.

The steps for fabrication of the device can include the following steps:
(1) forming a polymeric tube using extrusion,
(2) radially deforming the formed tube,
(3) forming a stent scaffolding from the deformed tube by laser machining a stent pattern in the deformed tube with laser cutting,
(4) optionally forming a therapeutic coating over the scaffolding,
(5) crimping the stent over a delivery balloon, and
(6) sterilization with election-beam (E-Beam) radiation.

In the extrusion step, a polymer is processed in an extruder above the melting temperature of the copolymer. In step (2) above, the extruded tube may be radially deformed to increase the radial strength of the tube, and thus, the finished stent and also to increase crystallinity. Detailed discussion of the manufacturing process of a bioabsorbable stent can be found elsewhere, e.g., U.S. Patent Publication Nos. 20070283552 and 20120073733.

The device body may include or may be coated with one or more therapeutic agents, including an antiproliferative, anti-inflammatory or immune modulating, anti-migratory, anti-thrombotic or other pro-healing agent or a combination thereof. The anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin I1, actinomycin X1, and actinomycin C1), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof.

The anti-inflammatory agent can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

These agents can also have anti-proliferative and/or anti-inflammatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable.

"Molecular weight refers to either number average molecular weight (Mn) or weight average molecular weight (Mw). References to molecular weight (MW) herein refer to either Mn or Mw, unless otherwise specified.

"Semi-crystalline polymer" refers to a polymer that has or can have regions of crystalline molecular structure and amorphous regions. The crystalline regions may be referred to as crystallites or spherulites which can be dispersed or embedded within amorphous regions.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

The "melting temperature" (Tm) is the temperature at which a material changes from solid to liquid state. In polymers, Tm is the peak temperature at which a semicrystalline phase melts into an amorphous state. Such a melting process usually takes place within a relative narrow range (<20° C.), thus it is acceptable to report Tm as a single value.

"Elastic deformation" refers to deformation of a body in which the applied stress is small enough so that the object retains, substantially retains, or moves towards its original dimensions once the stress is released.

The term "plastic deformation" refers to permanent deformation that occurs in a material under stress after elastic limits have been exceeded.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" and "stiffness" may be defined as the ratio of a component of stress or force per unit area applied to a material divided by the strain along an axis of applied force that results from the applied force. The modulus or the stiffness typically is the initial slope of a stress—strain curve at low strain in the linear region. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Elongation at break" is the elongation recorded at the moment of rupture of a specimen in a tensile elongation test, expressed as a percentage of the original length or the strain.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical device implantable within a peripheral vessel of the body, comprising:
   a cylindrical radially expandable body formed from a polymer formulation comprising a bioresorbable elastic material greater than 60 wt % of the body and a bioresorbable rigid material less than 40 wt % of the body which form rigid domains dispersed throughout a matrix of the elastic material, and
   an anti-restenosis drug associated with the body for delivery to the vessel upon implantation of the medical device in the peripheral vessel,
   wherein the elastic material has a glass transition temperature (Tg) <25 deg C. and the rigid material has a Tg greater than 37 deg C., and
   wherein the body is configured to be expanded from a crimped state to an expanded state within the peripheral vessel in contact with the vessel wall.

2. The device of claim 1, wherein the elastic material comprises elastic polymer or segments selected from the group consisting of poly(4-hydroxybutyrate) (P4HB), polycaprolactone, (PCL) poly(trimethylene carbonate) (PTMC), poly(butylene succinate) (PBS), and poly(p-dioxanone) (PDO).

3. The device of claim 1, wherein the rigid material comprises rigid polymer or segments selected from the group consisting of poly(L-lactide) (PLLA), polyglycolide (PGA) and poly(L-lactide-co-glycolide) (PLGA).

4. The device of claim 1, wherein the polymer formulation is a polymer blend of an elastic polymer as the elastic material and a block or random copolymer including rigid polymer segments as the rigid material and elastic polymer segments, wherein the elastic polymer of the blend includes PCL, PTMC, PDO, or P4HB, the rigid polymer segments of the copolymer include PLLA or PGA, and the elastic polymer segments of the copolymer include PCL, PTMC, PDO, or P4HB.

5. The device of claim 1, wherein the polymer formulation is a polymer blend of an elastic polymer as the elastic material, a rigid polymer as the rigid material, and a block copolymer less than 5 wt % of the body including elastic polymer segments and rigid polymer segments corresponding to the elastic polymer and the rigid polymer, respectively, which acts as compatibilizer between the elastic polymer and the rigid polymer, wherein the elastic polymer includes PCL, PTMC, PDO, or P4HB, the rigid polymer segments of the copolymer include PLLA or PGA.

6. The device of claim 1, wherein the polymer formulation is a polymer blend of an elastic block or random copolymer including elastic polymer segments as the elastic material and rigid polymer segments and a rigid polymer as the rigid material, wherein the elastic polymer segments of the copolymer include PCL, PTMC, PDO, or P4HB, the rigid polymer segments of the copolymer include PLLA or PGA, and the rigid polymer includes PLLA or PGA.

7. The device of claim 1, wherein the polymer formulation is a block copolymer including an elastic polymer segment as the elastic material and a rigid polymer segment as the rigid material, wherein the elastic polymer segments of the copolymer include PCL, PTMC, PDO, or P4HB and the rigid polymer segments of the copolymer include PLLA or PGA.

8. The device of claim 1, wherein the elastic material has an elongation at break of greater than 50% and modulus of elasticity of less than 1 GPa.

9. The device of claim 1, wherein the rigid material has an elongation at break of less than 5% and modulus of elasticity of greater than 3 GPa.

10. The device of claim 1, wherein a radial strength of the device is 10 to 150 mm Hg.

11. The device of claim 1, wherein a crush recovery of the device is such that the device attains greater than about 80% or 90% of its diameter after being crushed to at least 50% of a pre-crush diameter.

12. The device of claim 1, wherein the device has an expanded diameter in an expanded state between 7 and 9 mm.

13. The device of claim 1, wherein when the device is expanded by a balloon to the expanded diameter, the device plastically deforms.

14. The device of claim 1, wherein when the device expands to the expanded diameter, the device self-expands and deforms elastically.

15. The device of claim 1, wherein the anti-restenosis drug comprises an anti-proliferative drug, anti-inflammatory drug, or both.

16. The device of claim 1, wherein a radial strength of the device in an expanded state is at most a radial pressure for the device to maintain contact with the vessel wall.

* * * * *